United States Patent
Sopori et al.

(10) Patent No.: US 7,420,669 B2
(45) Date of Patent: Sep. 2, 2008

(54) OPTIC PROBE FOR SEMICONDUCTOR CHARACTERIZATION

(75) Inventors: Bhushan L. Sopori, Denver, CO (US); Artak Hambarian, Yerevan (AM)

(73) Assignee: Midwest Research Institute, Kansas City, MO (US)

( * ) Notice: Subject to any disclaimer, the term of this patent is extended or adjusted under 35 U.S.C. 154(b) by 484 days.

(21) Appl. No.: 10/543,970

(22) PCT Filed: Jul. 1, 2004

(86) PCT No.: PCT/US2004/021240

§ 371 (c)(1),
(2), (4) Date: Jul. 28, 2005

(87) PCT Pub. No.: WO2006/014152

PCT Pub. Date: Feb. 9, 2006

(65) Prior Publication Data

US 2007/0145995 A1     Jun. 28, 2007

(51) Int. Cl.
  *G01N 21/00* (2006.01)
(52) U.S. Cl. ............... 356/237.4; 356/237.1; 356/237.5
(58) Field of Classification Search ... 356/237.1–241.6, 356/426–431, 600–640
See application file for complete search history.

(56) References Cited

U.S. PATENT DOCUMENTS

| | | | |
|---|---|---|---|
| 4,295,162 A | 10/1981 | Carlsen | |
| 4,314,763 A | 2/1982 | Steigmeier et al. | |
| 4,583,861 A * | 4/1986 | Yamaji et al. | 356/446 |
| 4,626,101 A | 12/1986 | Ogawa et al. | |
| 4,732,473 A | 3/1988 | Bille et al. | |
| 4,735,504 A * | 4/1988 | Tycko | 356/336 |
| 4,794,265 A * | 12/1988 | Quackenbos et al. | 250/559.45 |
| 5,389,794 A * | 2/1995 | Allen et al. | 250/559.48 |
| 5,513,162 A | 4/1996 | Kishi et al. | |
| 5,883,714 A * | 3/1999 | Jann et al. | 356/484 |
| 6,104,481 A * | 8/2000 | Sekine et al. | 356/237.5 |
| 6,130,871 A | 10/2000 | Watabe | |
| 6,201,601 B1 * | 3/2001 | Vaez-Iravani et al. | 356/237.4 |
| 6,515,742 B1 * | 2/2003 | Ruprecht | 356/237.4 |
| 6,538,730 B2 * | 3/2003 | Vaez-Iravani et al. | 356/237.2 |
| 6,559,937 B2 | 5/2003 | Tamada et al. | |
| 6,608,676 B1 | 8/2003 | Zhao et al. | |
| 7,061,598 B1 * | 6/2006 | Bevis et al. | 356/237.1 |
| 7,102,744 B2 * | 9/2006 | Marxer et al. | 356/237.3 |
| 7,295,299 B2 * | 11/2007 | Schmalfuss | 356/237.2 |
| 2001/0048523 A1 | 12/2001 | Fossey et al. | |

(Continued)

FOREIGN PATENT DOCUMENTS

JP     1053138     3/1989

(Continued)

*Primary Examiner*—Gregory J. Toatley, Jr.
*Assistant Examiner*—Jarreas C Underwood
(74) *Attorney, Agent, or Firm*—Paul J. White

(57) ABSTRACT

Described herein is an optical probe (120) for use in characterizing surface defects in wafers, such as semiconductor wafers. The optical probe (120) detects laser light reflected from the surface (124) of the wafer (106) within various ranges of angles. Characteristics of defects in the surface (124) of the wafer (106) are determined based on the amount of reflected laser light detected in each of the ranges of angles. Additionally, a wafer characterization system (100) is described that includes the described optical probe (120).

28 Claims, 5 Drawing Sheets

U.S. PATENT DOCUMENTS

| | | |
|---|---|---|
| 2002/0036771 A1 | 3/2002 | Sato et al. |
| 2002/0097393 A1 | 7/2002 | Nikoonahad et al. |
| 2002/0191179 A1 | 12/2002 | Tukker et al. |
| 2003/0103203 A1 | 6/2003 | Isozaki et al. |

FOREIGN PATENT DOCUMENTS

| | | |
|---|---|---|
| JP | 4282846 | 10/1992 |

\* cited by examiner

OPTIC PROBE FOR SEMICONDUCTOR CHARACTERIZATION

GOVERNMENT CONTRACT

The United States Government has rights in this invention under Contract No. DE-AC36-99GO10337 between the United States Department of Energy and the National Renewable Energy Laboratory, a Division of the Midwest Research Institute.

TECHNICAL FIELD

Semiconductor device manufacturing routinely includes characterization of wafers and devices as a part of process monitoring. The characterization involves measurement of a broad range of physical and electronic parameters such as defects, thickness, surface morphology, line-width, step height, surface charge, dopant concentration, resistivity or sheet rho. For the last two decades there has been increasing emphasis on developing non-contact techniques for characterization of the entire wafer.

Most current approaches for material/device characterization are based on non-contact, optical methods in which the entire wafer or device is mapped. Typically, the wafer is illuminated with a light beam that scans the wafer and the signal (such as reflected light, light beam induced current or voltage) is measured. Many methods for scanning have been developed, which are typically categorized into two types, moving beam scanning and moving wafer scanning.

Moving beam scanning has the advantage of speed. Moving beam scanning of wafers can be done very quickly. However, moving beam scanning typically suffers from beam distortion and changes in the reflectance with angle of incidence. Moving wafer scanning typically performs better with respect to beam distortion and changes in the reflectance with angle of incidence than moving beam scanning because it does not suffer from beam distortions. However, moving wafer scanning is typically very slow, because it requires changes in the direction of the moving wafer/stage (of a large momentum) during scanning.

SUMMARY

Described herein are various implementations of an optical probe for use in characterizing surface defects in wafers, such as semiconductor wafers. The optical probe focuses light on the wafer and detects light reflected from the surface of the wafer within various ranges of angles. Additionally, described herein are various implementations of a wafer characterization system that includes the described optical probe. The wafer characterization system includes, among other things, mechanisms for holding and rotating a wafer and a mechanism for positioning the probe at various locations above the surface of the wafer. Characteristics of defects in the surface of the wafer are determined by the wafer characterization system based on the amount of reflected light detected by the optical probe in the various ranges of angles.

DETAILED DESCRIPTION

Described herein are various systems for characterizing wafers, such as semiconductor wafers. In accordance with these systems and methods, wafer characterization is carried out on a rotating wafer using an optical probe that is moved radially across the surface of the wafer in predefined steps. Defect characterization is performed on the wafer at each step.

In accordance with various implementations described herein, in one implementation the wafer is spun at a constant rotational speed (i.e., a constant angular velocity). As the wafer is spinning, an optical probe is positioned above the surface of the wafer at a given radial position. The optical probe, which includes a light source (e.g., a laser) and detection optics, illuminates the surface of wafer and detects light that is reflected or scattered from the surface of the wafer. This reflected light may have specular, near-specular, and diffused components. The optical probe includes various mechanisms for detecting the specular, near-specular, and/or diffused components within the reflected light.

In another implementation, the rotational speed of the wafer may be changed so that the rotational speed can be tailored as a function of radial displacement of the probe (i.e., a constant linear velocity). In yet other implementations, other schemes for moving the probe relative to wafer and/or rotating the wafer may be used.

The type of a defect detected on the surface of the wafer may be determined based on the specular, near-specular, and/or diffused components detected within the reflected light. For example, in the absence of any defects, the detected light will have only a specular component. However, when defects are present in the illuminated region, the detected light will include near-specular and/or defuse components. The contribution of each component in the detected light depends upon the type and density of defects present in the surface of the wafer. In particular, the presence of near-specular components in the detected light implies the presence of a scratch-like defect or defects on the surface of the wafer in the illuminated region. The presence of diffuse components in the detected light implies one or more particulate material defect on the surface of the wafer in the illuminated region. The intensity of the near-specular and/or diffuse components in the detected light is proportional to the number of defects within the illuminated region.

Figure 1:
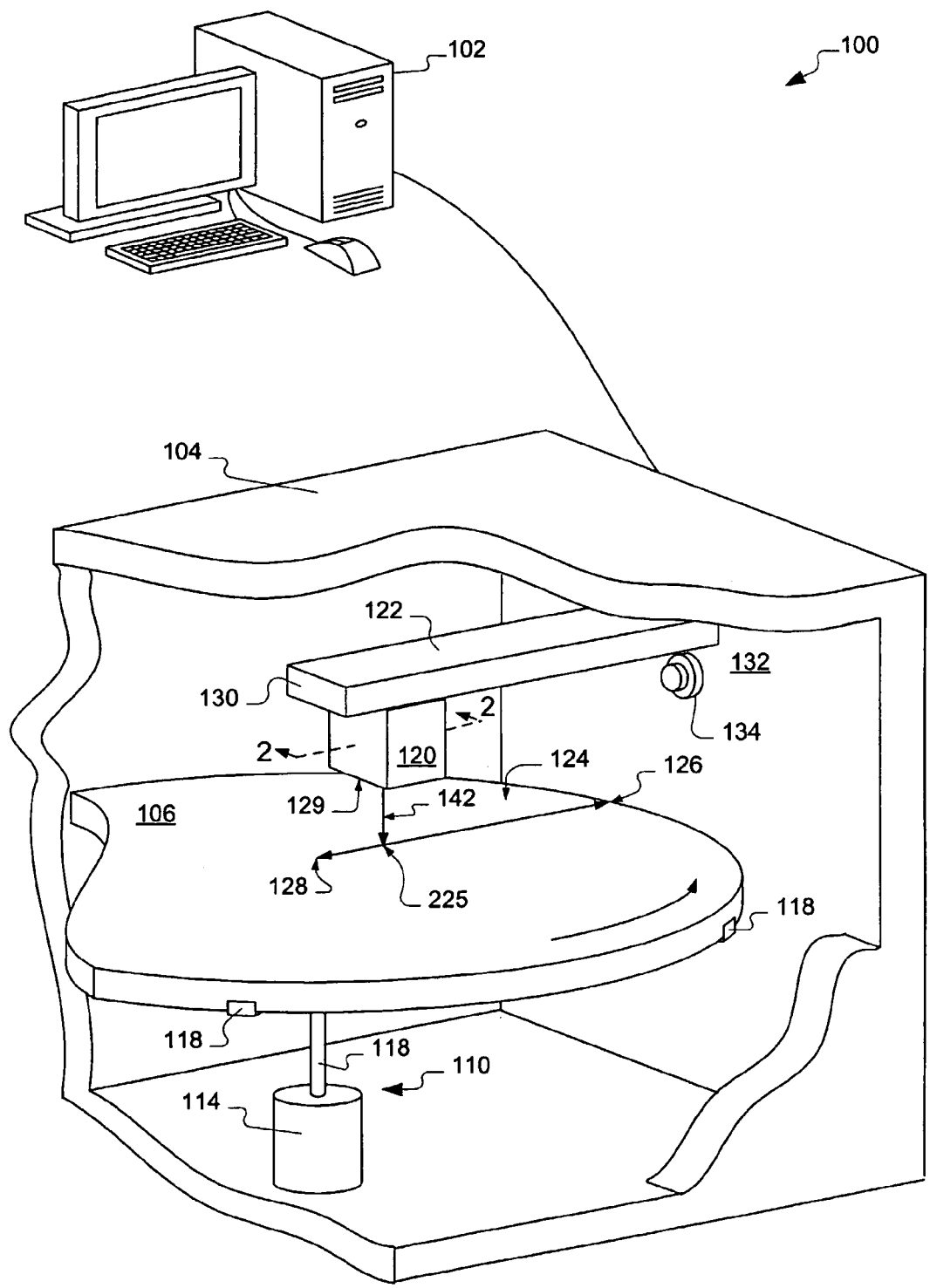
FIG. 1 illustrates an implementation of a semiconductor wafer characterization system.

Turning now to FIG. 1, illustrated therein is an exemplarily wafer characterization system 100. As shown, the wafer characterization system 100 includes a computer system 102 operably connected to a chamber 104. The chamber 104 includes various electrical and mechanical mechanisms, each of which are described below, that are used to characterize a semiconductor wafer 106 held within the housing. The computer system 102, also described in detail below, includes appropriate software, hardware, and/or firmware for receiving and processing signals received from the chamber 104 and for controlling the various electrical and mechanical mechanisms of chamber 104.

The chamber 104 is shown in cutaway view in FIG. 1 so that the various mechanisms housed therein and the wafer 106 can be seen. In general, the chamber 104 comprises an enclosure that is operable to house a wafer rotation mechanism 110, a wafer 106, an optical probe 120, and a probe translation mechanism 122. While the chamber 104 is shown in FIG. 1 as being box shaped (rectangular prism), the chamber 104 may have any of a variety of shapes or configurations. While not shown in FIG. 1, the chamber 104 includes some mechanism (e.g., a door or opening) by which a wafer 106 may be placed within the chamber 104. In some implementations the chamber 104 may be sealed in a manner that prevents or minimizes the entry of contaminants (e.g., dust or the like) while wafer characterization is being performed. The chamber 104 may also include various systems for further controlling the environment within the chamber 104.

As described, housed within the chamber 104 is a wafer rotation mechanism 110. The wafer rotation mechanism 110 supports and rotates the wafer 106 within the chamber 104. The wafer rotation mechanism 110 may generally be any mechanism or mechanisms that is/are operable to support and rotate the wafer 106 within the chamber 104 at a desired rotational speed. For example, in the implementation shown, the wafer rotation mechanism 110 includes a motor 114 and a wafer support mechanism 118. The wafer support mechanism 118 holds the wafer 106 and is operably connected to the motor 114 in such a manner that the motor 114 causes rotation of the wafer 106.

Those skilled in the art will appreciate that there are a number of wafer rotation mechanisms available. Furthermore, those skilled in the art will appreciate that wafer rotation mechanisms may use various configurations and types of wafer support mechanisms 118 and motors 114. For example, and without limitation, in one implementation the wafer support mechanism 118 comprises a vacuum (wafer) chuck. In another implementation the wafer support mechanism 118 comprises an edge handling chuck. Furthermore, the wafer support mechanism may include a mechanism for aligning the wafer (e.g., an edge aligner). However, it is envisioned that any number of available (now or in the future) wafer support mechanisms 118 may be used to support that wafer 106.

In one implementation the motor 114 comprises a synchronous motor that has the capability for positioning feedback (such as an optical encoder/decoder). However, it is envisioned that any number of available (now or in the future) motors may be used in the wafer rotation mechanism 110. In one implementation, the operational parameters of the motor (e.g., rotational speed, torque, starting, stopping, etc.) are controlled by the computer system 102.

Also included in the chamber 104 are an optical probe 120 and a probe translation mechanism 122. Operationally, the probe translation mechanism 122 supports and moves the optical probe 120 adjacent to the surface 124 of the wafer 106. More particularly, the probe translation mechanism 122 is operable to move the optical probe 120 adjacent to the surface 124 of the wafer 106 between a position at or near the outer radius 126 of the wafer 106 and a position at or near the center 128 of the wafer 106.

Generally, the probe translation mechanism 122 may use any of a number of mechanisms to position the probe above and adjacent the surface 124. For example, and without limitation, FIG. 1 illustrates an implementation of the probe translation mechanism 122 in which the optical probe 120 is supported from, and moved along, an arm 130 positioned above the surface 124 of the wafer 106. In accordance with one variation of this implementation, the arm 130 extends from an inner wall 132 of the chamber 104 out over the surface 124 of the wafer 106. In this implementation, the optical probe 120 is moved along the arm 130 between a position at or near the outer radius 126 of the wafer 106 to a position near the center 128 of the wafer 106.

The optical probe 120 may be moved along the arm 130 using a variety of mechanisms. For example, in one implementation the optical probe 120 is moved along the arm 130 by a motor and a mechanism that converts the rotary motion of the motor to a linear motion of the optical probe 120 along the arm 130. For example, and without limitation, in one implementation the optical probe 120 is moved along the arm 130 by a linear actuator including a stepper motor.

In accordance with one implementation, the probe translation mechanism 122 supports and moves the optical probe 120 in a substantially parallel manner relative to the surface 124 of the wafer 106, such that the optical probe 120 maintains a constant distance from the surface 124 of the wafer 106. The distance between the bottom 129 of the optical probe 120 and the surface 124 of the wafer 106 may vary, depending on various operational parameters, such as the relative smoothness of the surface 124 of the wafer and various optical properties of the optical probe 120. For example, in the case where the surface of the wafer 106 is highly polished, the distance between the bottom 129 of the optical probe 120 and the surface 124 of the wafer 106 may be on the order of about a millimeter. In contrast, in the case where the surface of the wafer 106 is relatively rough, the distance between the bottom 129 of the optical probe 120 and the surface 124 of the wafer 106 may be on the order of about a few millimeters, or more.

In general, the optical probe 120 performs two functions, focusing a light beam 142 onto the surface 124 of the wafer 106 and collecting light that is reflected off the surface 124 of the wafer 106. More particularly, the optical probe 120 is operable to collect three categories of reflected light, each of which are discussed in detail below. Before proceeding with a detailed discussion of these three categories of reflected light, a general discussion of various terminology used in discussing reflected light will first be presented.

As will be appreciated to those skilled in the art, light that strikes the surface 124 of the wafer 106 at a given point, which we will call the reflection point 225, is referred to as incident light (or incident beam). The light that leaves the surface 124 of the wafer 106 from the reflection point 225 is referred to as a reflected light. In this context, an imaginary line may be envisioned that extends from the surface 124 of the wafer 106 at the reflection point 225, and which is perpendicular to the surface 124 of the wafer 106. This line is referred to as the normal line. The angle between the incident ray and the normal line is referred to as the angle of incidence, or the incident angle. The angle between the reflected ray and the normal line is referred to as the angle of reflection, or the reflected angle.

Reflected light may be categorized according to its angle of reflection. In general, the angle of reflection for reflected light is dependent on the size of irregularities in or on the surface 124 of the wafer 106 at the point of reflection. If the size of irregularities in or on the surface 124 of the wafer 106 at the point of reflection is small, (i.e., the surface is smooth) the reflected light will have an angle of reflection that is equal to the angle of incidence. This type of reflected light is referred to as specular reflected light ("specular light"). In contrast, if irregularities in the surface 124 of the wafer 106 are large, the reflected light will have an angle or angles of reflection that is/are not equal to the angle of incidence. That is, the reflected light will be scattered of the surface 124 at various angles of incidence. This type of reflected light is referred to as diffuse reflected light ("diffuse light").

With respect the systems and methods described herein, three types of reflected light are defined: specular light, near-specular light, and diffuse light. These three types of light are categorized according to their angles of reflection, or in terms of ranges of angles of reflection. It will be appreciated that these ranges of angles of reflection may be selected for each of the specular light, near-specular light, and diffuse light according to various design and implementation constraints. The ranges of angles of reflection for each of the specular light, near-specular light, and diffuse light may be discrete with respect to ranges for others of the three types of reflected light. The ranges of angles of reflection for each of the specular light, near-specular light, and diffuse light may also overlap a range of angles of reflection for another type of reflected light. Additionally, in some cases there may be gaps in ranges of angles of reflection.

As such, while particular ranges will now be described herein with respect to various implementations of the optical probe, it is not intended that the optical probe 120 is necessarily limited to the ranges defined in these specific implementations.

In accordance with one implementation, the range of angles of reflection for specular light is between approximately plus or minus three degrees and five degrees of reflection (±3-5°). In accordance with one implementation, the range of angles of reflection for near-specular light is between plus or minus five degrees and fifteen degrees of reflection (±5-15°). In accordance with one implementation, the range of angles of reflection for diffuse light is greater than approximately 15 degrees of reflection ($\geqq\approx 15°$).

The manner in which the angels of reflection of the specular, near-specular, and diffuse light are defined, in terms of their detection, may vary. However, as described below, in accordance with at least some implementations, these ranges of angles are defined by the physical dimensions and/or positions of the various mechanisms that are used within the optical probe to direct and detect the reflected light.

Figure 2:
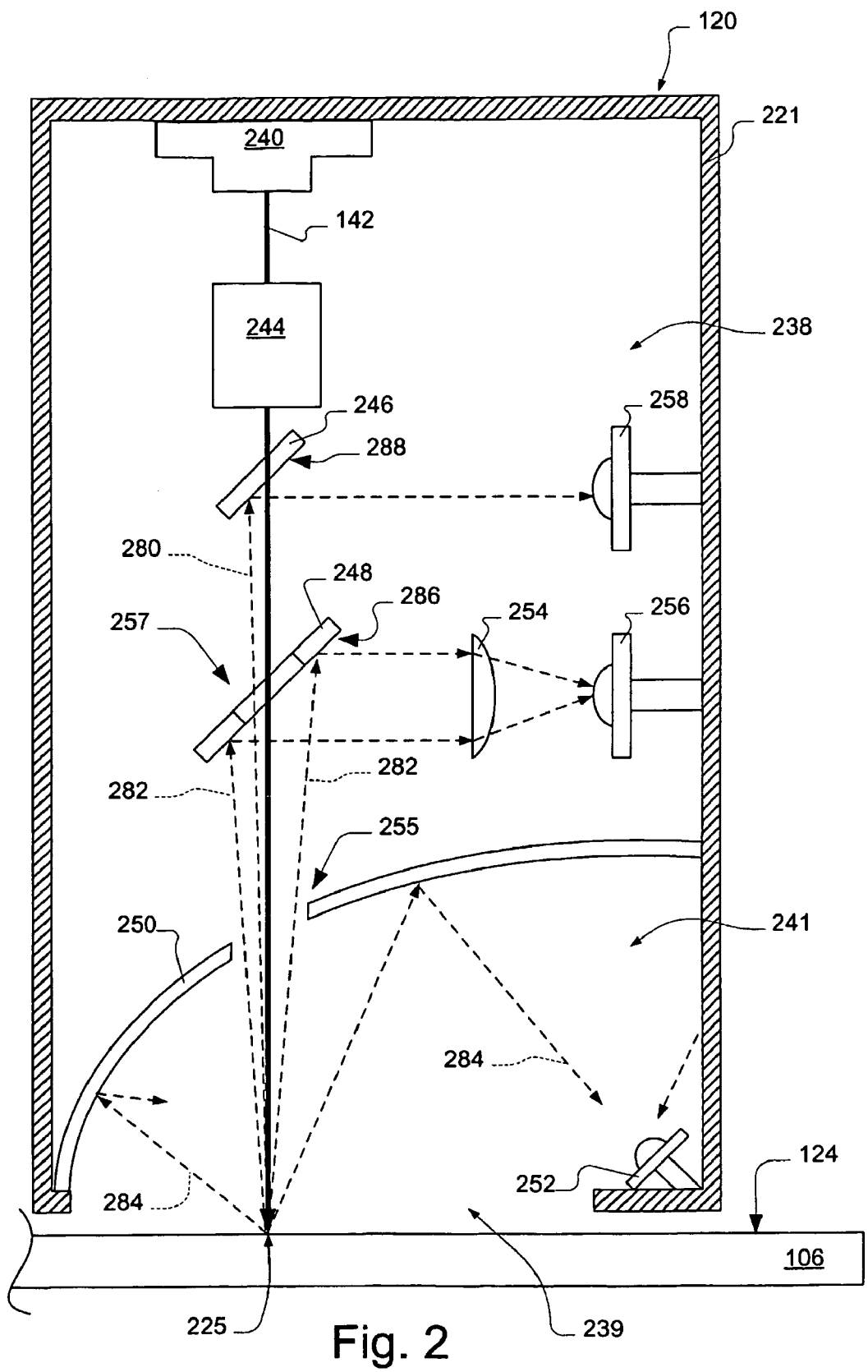
FIG. 2 illustrates an implementation of an optical probe shown in FIG. 1.

Turning now to FIG. 2, illustrated therein is one implementation of the optical probe 120 shown in a cut-away view taken along 2-2 in FIG. 1. As will now be described, the optical probe 120 includes various mechanisms for collecting and/or detecting light reflected from the surface 124 of the wafer in the range of angles of reflected light described above. It should be appreciated that while the various mechanisms of the optical probe operate to collect and/or detect light reflected from the surface 124 of the wafer, the optical probe will typically not collect all of the light reflected from the surface 124 of the wafer 106.

As shown, the optical probe 120 includes a housing 221 an internal cavity 238 and a lower probe aperture 239 through which incident light is transmitted to, and reflected light is collected from, the wafer 106. Included in the internal cavity 238 are a light source 240, beam focusing optics 244, a beam splitter 246, an annular mirror 248, a diffuse light collector 250, a diffuse light detector 252, a near-specular focusing lens 254, a near-specular light detector 256, and a specular light detector 258, each of which will now be described.

In general, the light source 240 may be any light source that is operable to produce a beam of light 142 that has a beam width of approximately 5 micrometers (5 μm) or smaller at the surface 124 of the wafer 106, or which is operable to produce a beam of light 142 that may focused by focusing optics 244 to a beam width of 5 micrometers (5 μm) or smaller at the surface 124 of the wafer 106.

In one implementation, the light source 240 comprises a laser light source. In such an embodiment, the laser light source ("laser") 240 may be any laser of a size and having dimensions appropriate for placement and operation, along with the other probe elements 244-256, within the internal cavity 238 of the optical probe 120. In one implementation the laser 240 comprises a Helium-Neon (HeNe) laser. In another implementation the laser 240 comprises a diode laser. In other implementations other types of lasers may be used, as will be clear to those skilled in the art.

Figure 3:
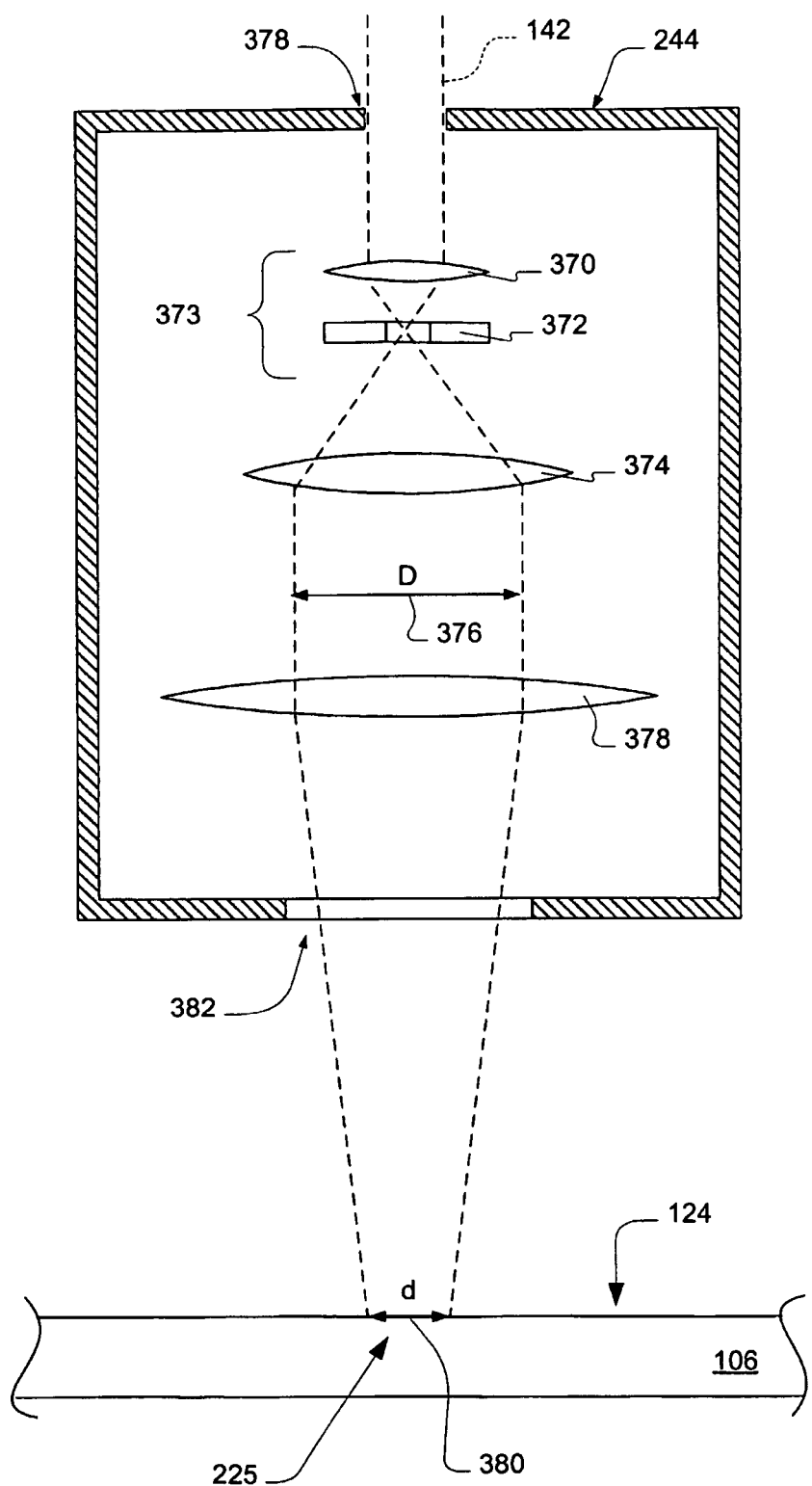
FIG. 3 illustrates an implementation of beam focusing optics shown in FIG. 2.

In general, the beam focusing optics 244 may be any device that is operable to fit within the cavity 238, along with the other probe elements, and that is operable to receive the laser beam 142 and focus, filter and/or otherwise process the laser beam 142. FIG. 3 illustrates one possible implementation of the beam focusing optics 244. The illustration of the beam focusing optics 244 in FIG. 3 shows only the beam focusing optics 244 and the wafer 106. For clarity, the other elements of the optical probe 120 are not shown in FIG. 3.

As shown, the beam focusing optics 244 includes a input lens 370, an aperture 372 (e.g., a pinhole screen), a collimating lens 374, and a focusing lens 378. In this implementation, the input lens 370 and the aperture 372 together form a spatial filter 373. In operation, the laser beam 142 enters the beam focusing optics 244 through an upper aperture 378. The laser beam 142 then passes through the spatial filter, which eliminates or minimizes off-axis or scattered light from the laser, and produces a smooth coherent beam diverging from the aperture 372.

Next, the laser beam 142 passes through the collimating lens 374, which collimates the beam 142. As shown in FIG. 3, the width of the laser beam 142 as it leaves the collimating lens 374 has a width (diameter) D 376. The collimated laser beam is then focused by the focusing lens 378. As shown, the laser beam passes through a lower aperture 382 and is focused at the reflection point 225 of the surface 124 of the wafer 106. The width (d) 380 of the laser beam 142 at the reflection point 225 may be determined using the following equation: $d = f \times \lambda / D$, where f is the focal length of the focusing lens 378 and λ is the wavelength of the laser light. For example, if a width (d) 380 of the laser beam 142 at the reflection point 225 of 5 μm is desired for a laser having a wavelength (λ) of 0.63 μm, and a width of 1.25 cm as it leaves the collimating lens 374, a focusing lens 378 having a focal length (f) of approximately 10 cm would be required.

Returning to FIG. 2, as shown, after leaving the beam focusing optics 244, the laser beam passes through the beam splitter 246, an annular mirror aperture 257 in the annular mirror 248, and a diffuse light collector aperture 255 in the diffuse light collector 250, before impinging on the wafer 106 at the reflection point 225.

As previously mentioned, the light beam hitting the surface 124 of the wafer 106 may be referred to as the incident beam and light that is reflected from the surface 124 of the wafer 106 may be referred to as reflected light. As also mentioned, reflected light may be classified into three types: specular light 280, near-specular light 282, and diffuse light 284, according to predefined ranges of angles of reflection. It should be appreciated that only a select few rays of reflected light are shown in FIG. 3 for the sake of clarity.

The detection of diffuse light 284 in the optical probe 120 illustrated in FIG. 3 is made using the diffuse light collector 250 and the diffuse light detector 252. In general, the diffuse light collector 250 functions to reflect some or all of the diffuse light 284 to the diffuse light detector 252. The manner in which the diffuse light collector 250 reflects diffuse light 284 to the diffuse light detector 252 may vary. However, in the implementation illustrated in FIG. 3, the diffuse light collector 250 comprises a portion of an elliptical dome structure that is concave relative to the lower probe aperture 239, and which has at least a portion of its lower surface 241 that is reflective to diffuse light 284.

In the implementation shown in FIG. 3, the light beam is focused to hit the surface 124 of the wafer 106 at a point that is not aligned with the axis of the elliptical dome structure of the diffuse light collector 250. In other implementations, the light beam may be focused to hit the surface 124 of the wafer 106 at other points relative to the axis of the elliptical dome structure. Furthermore, in other implementations the diffuse light collector 250 may have other shapes. The interior surface 241 is reflective, such that diffuse light 284 that strikes the interior surface 241 is reflected toward the diffuse light detector 252.

The diffuse light detector 252 may comprise any light detector that is operable to detect the diffuse light 284 and provide an electrical signal that is representative of the intensity of the detected diffuse light 284. For example, and without limitation, in one implementation, the diffuse light detector 252 comprises one or more silicon photodiodes and/or one or more photomultiplier tubes, with a suitable amplifier or amplifiers for amplifying the electrical signal.

As previously noted, diffuse light 284 may be defined in terms of a range of angles of reflection from the surface 124 of the wafer 106. In this implementation, the lower limit of the range of angles for diffuse light 284 is set or defined by the size and shape of the reflective portion of the lower surface 241 of the diffuse light collector 250. In the case where the entire lower surface of the diffuse light collector 250 is reflective to diffuse light, the lower limit of the range of angles for diffuse light 284 is set or defined by the size and shape of the diffuse light collector aperture 255. In such a case, the upper limit of the range of angles for diffuse light 284 is set or defined by the shape and dimensions of the lower probe aperture 239 of the optical probe 120.

The detection of near-specular light 282 in the optical probe 120 illustrated in FIG. 3 is made using the annular mirror 248, the near-specular focusing lens 254, and the near-specular light detector 256. In accordance with one implementation, the annular mirror 248 comprises an annular disc having a substantially circular outer radius and a substantially circular annular aperture 257. At least a portion of the lower surface 286 of the annular mirror 248 will be reflective to near-specular light 282 that impinges on the lower surface 286.

The lower surface 286 of the annular mirror 248 is positioned relative to the near-specular focusing lens 254 and the near-specular detector 256, such that near-specular light 282 reflected from the lower surface 286 of the annular mirror 248 will be reflected substantially toward the near-specular focusing lens 254. The near-specular focusing lens then operates to focus the near-specular light 282 onto the near-specular detector 256.

The near-specular detector 256 may comprise any light detector that is operable to detect the near-specular light 282 and provide a signal that is representative of near-specular light 282 detected at the near-specular detector 256. For example, and without limitation, in one implementation, the near-specular detector 256 comprises one or more Si photodiodes and/or one or more photomultiplier tubes, with a suitable amplifier or amplifiers for amplifying the detected signal.

As with the diffuse light 284, the near-specular light 282 may be defined in terms of a range of angles of reflection from the surface 104 of the wafer 106. In this implementation, the upper and lower limits of the range of angles for near-specular light 282 is set or defined by the shape and size of the portion of the annular mirror 248 that is reflective to near-specular light and/or the diffuse light collector aperture 255. In the case where the entire lower surface of the annular mirror 248 is reflective near-specular light, the lower limit of the range of angles for near-specular light 282 is set or defined by the shape and size of the annular aperture 257 and/or the diffuse light collector aperture 255. In this case, the upper limit of the range of angles for near-specular light 282 is set or defined by the shape and size of the outer perimeter of the annular mirror 248.

The detection of specular light 280 in the optical probe 120 illustrated in FIG. 3 is made using the beam splitter 246 and the specular light detector 258. In accordance with one implementation, the beam splitter 246 comprises an a one-way mirror, sometimes called a two-way mirror, which includes a lower surface 288, at least a portion of which is reflective to specular light 280.

In operation, the beam splitter 246 allows a portion of the light of the laser beam 142 to pass there through as the laser beam 142 is being shinned onto the surface 124 of the wafer 106, and reflects a portion of the specular light 280 that is reflected from the surface 124 of the wafer 106. The lower surface of the beam splitter 246 will be positioned relative to the specular detector 258 such that light reflected from the lower surface 288 will be reflected substantially toward the specular detector 258.

The specular detector 258 may comprise any light detector that is operable to detect the specular light 280 and provide a low noise electrical signal. The precise choice of the detector may depend on the laser wavelength and its power. For example, and without limitation, in one implementation, the specular detector 258 comprises one or more high-sensitivity Si photodiodes and/or one or more photomultiplier tubes, with a suitable amplifier or amplifiers for amplifying the signal from the detector 258. The specular detector 258, the near-specular detector 256 and the diffuse detector 252 may be identical or different in construction and/or operation.

As with the diffuse light 284 and the near-specular light 282, the specular light 280 may be defined in terms of a range of angles of reflection from the surface 124 of the wafer 106. In this implementation, the upper and lower limits of the range of angles for specular light 280 is set or defined by the size and shape of the reflective portion of the lower surface 288 of the beam splitter 246. In the case where the entire surface of the beam splitter 246 is reflective to specular light, the lower limit of the range of angles for specular light 280 is zero. In this case, the upper limit of the range of angles for diffuse light 284 is set or defined by the shape and dimensions of the outer circumference of the lower surface 288 of the beam splitter 246.

Figure 4:
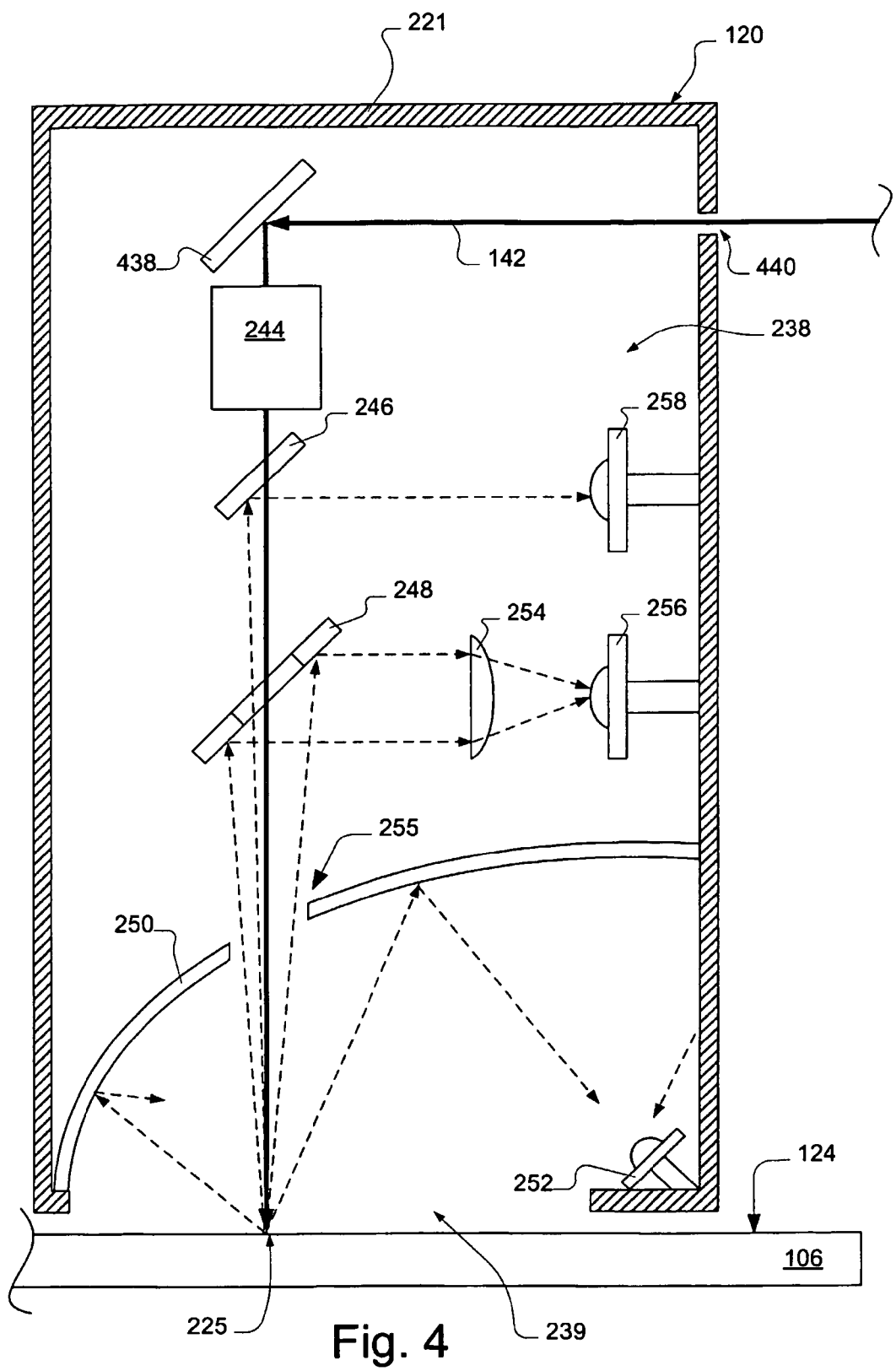
FIG. 4 illustrates another implementation of the optical probe shown in FIG. 1.

Turning now to FIG. 4, illustrated therein is another implementation of the optical probe 120, shown in a cut-away view taken along 2-2 in FIG. 1. As will be appreciated, many of the components of the optical probe illustrated in FIG. 4 are identical to the components in optical probe 120 illustrated in FIG. 2, as indicated by identical reference numerals. The primary difference between the implementations of the optical probe 120 shown in FIGS. 2 and 4 relates to location of light sources for the optical probe. In this respect, the optical probe implementation illustrated in FIG. 2 includes a light source 240 within the optical probe 120. In contrast, the optical probe implementation illustrated in FIG. 4 does not include a light source within the optical probe 120. Rather, the optical probe implementation illustrated in FIG. 4 includes mirror 438 for reflecting light originating from a light source 134 (shown in FIG. 1) located externally to the optical probe 120. Additionally, the optical probe implementation illustrated in FIG. 4 includes a side aperture 440, through which the laser beam 142 enters the cavity 238.

In all other aspects, the optical probe 120 illustrated in FIG. 4 is identical in form and function to the optical probe 120 illustrated in FIG. 2, including the form and function of the various elements 244-258 that are common to both optical probes.

It should be appreciated that while the optical probe 120 is shown herein as being box shaped (a rectangular prism), the optical probe 120 may have any of a variety of shapes. Likewise, the overall size of the optical probe 120 may vary. In accordance with one implementation, and without limitation, the optical probe 120 has the form of a rectangular prism, which has dimensions on the order of approximately four inches by four inches by six inches.

Figure 5:
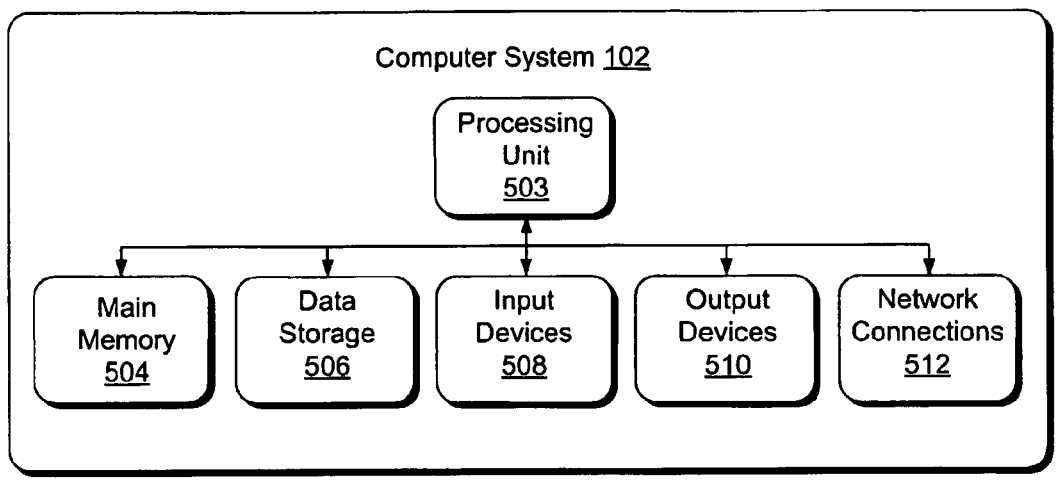
FIG. 5 illustrates an implementation of a computer system shown in FIG. 1.

Turning now to FIG. 5, illustrated therein is one possible implementation of the computer system 102 illustrated in FIG. 1. The computing system 102 illustrated in FIG. 5 is configured as a personal computer (PC). However, the computing system 102 may also assume a variety of other configurations.

The computer system 102 includes appropriate hardware, software, and/or firmware for controlling various electrical and mechanical mechanisms of the chamber 104. Additionally, in various implementations, computer system 102 includes appropriate hardware, software, and/or firmware for performing operations related to semiconductor wafer surface characterization.

In its most basic configuration, the computing system 102 includes a processing unit 503 and main memory 504, which may include both volatile and/or non-volatile memory. Additionally, the computing system 102 may include or have access to various data storage devices or systems 506, including various removable and/or non-removable mass storage devices. Examples of mass storage devices are, without limitation, various magnetic, optical, and/or non-volatile semiconductor memory, etc. In the case where the data storage device 506 comprises a number of storage devices, those devices may be distributed, such as across a computer network.

The memory 504 and the data storage device(s) 506 contain or comprise computer-readable media. In general, computer-readable media may include, without limitation, both volatile and nonvolatile memory, mass storage devices, removable and non-removable media, and modulated data signals. The term "modulated data signal" refers to a signal that has one or more of its characteristics set or changed in such a manner as to encode information in the signal.

The computing system 102 may have input devices 508, such as a keyboard, a pointing device (mouse), and various hardware for interfacing with the chamber 104. For example, and without limitation, such input devices 508 may comprise various interface circuits or devices for controlling the movement of the optical probe 120, for controlling the motor 114, and for receiving or otherwise capturing and/or processing signals from the various light detectors 252, 256, and 258.

The computing system 102 may also have various output devices 510, such as display devices, speakers, printers, or various other computer output devices. Other aspects of the computing system 102 may include network or communications connections 512, to other devices, computers, networks, servers, etc., using either wired or wireless computer-readable media.

As noted, the computer system 102 may include appropriate software for controlling the operations of the chamber 104 and/or for performing semiconductor wafer surface characterization. Such software will typically include computer-executable instructions, various routines, programs, objects, components, data structures, etc., that perform particular tasks or operations and/or implement particular abstract data types, each or all of which may be embodied in or on a computer readable medium.

Although some exemplary methods and systems have been illustrated in the accompanying drawings and described in the foregoing Detailed Description, it will be understood that the methods and systems shown and described herein are not limited to the particular implementations described, but rather are capable of numerous rearrangements, modifications and substitutions without departing from the spirit of the inventions set forth and defined by the following claims.

The invention claimed is:

1. A wafer characterization system, comprising:
a chamber;
a wafer rotation mechanism operable to rotate a wafer within the chamber;
an optical probe including laser focusing optics operable to focus laser light on a surface of the wafer and a laser light detection mechanism operable to detect laser light reflected from the surface of the wafer; and
a probe translation mechanism operable to move the optical probe adjacent the surface of the wafer; and
wherein the laser light detection mechanism includes:
a diffuse light detector and a diffuse light director directing only diffuse reflected laser light from the surface of the wafer to the diffuse light detector;
a near specular light detector and a near-specular light director directing only near-specular reflected laser light from the surface of the wafer to the near-specular light detector; and
a specular light detector and a specular light director directing only specular reflected laser light from the surface of the wafer to the specular light detector.

2. The wafer characterization system recited in claim 1, further comprising an annular mirror, a focusing lens, and a near-specular light detector, wherein the annular mirror reflects near-specular reflected laser light from the surface of the wafer through the focusing lens to the near-specular light detector.

3. The wafer characterization system recited in claim 1, wherein the laser focusing optics include a spatial filter.

4. The wafer characterization system recited in claim 1, wherein the laser focusing optics include an input lens, a pinhole screen, a collimating lens, and a focusing lens, wherein the laser light passes, in order, through the input lens, the pinhole screen, the collimating lens, and the focusing lens.

5. The wafer characterization system recited in claim 1, wherein the probe translation mechanism includes an arm portion within the chamber, and wherein the arm portion includes a mechanism that moves the optical probe adjacent the surface of the wafer.

6. The wafer characterization system recited in claim 1, wherein the probe translation mechanism includes an arm portion including a stepper motor for moving the optical probe adjacent the surface of the wafer.

7. The wafer characterization system recited in claim 1, wherein the probe translation mechanism includes a linear actuator for moving the optical probe adjacent the surface of the wafer.

8. The wafer characterization system recited in claim 1, wherein the probe translation mechanism includes a linear actuator incorporating a stepper motor for moving the optical probe adjacent the surface of the wafer.

9. The wafer characterization system recited in claim 1, wherein the wafer rotation mechanism includes a motor operably connected a wafer support mechanism.

10. The wafer characterization system recited in claim 1, wherein the wafer rotation mechanism includes a vacuum chuck.

11. The wafer characterization system recited in claim 1, wherein the wafer rotation mechanism includes synchronous motor and a vacuum chuck.

12. An optical probe, comprising:
laser focusing optics operable to focus laser light on a surface of a wafer; and
a laser light detection mechanism operable to detect laser light reflected from the surface of the wafer in three ranges of angles of reflection; and
wherein the laser light detection mechanism includes:
a diffuse light detector; a diffuse light collector that reflects only diffuse reflected laser light from the surface of the wafer to the diffuse light detector;
a near specular light detector; an annular mirror that reflects only near-specular reflected laser light from the surface of the wafer to the near-specular light detector;
a specular light detector; and
a beam splitter that reflects only specular reflected laser light from the surface of the wafer to the specular light detector.

13. The optical probe recited in claim 12, further comprising a laser light source to produce the laser light.

14. The optical probe recited in claim 12, further comprising a Helium-Neon laser that produces the laser light.

15. The optical probe recited in claim 12, further comprising a diode laser to produce the laser light.

16. The optical probe recited in claim 12, wherein the laser focusing optics includes a spatial filter.

17. The optical probe recited in claim 12, wherein the laser focusing optics include an input lens, a pinhole screen, a collimating lens, and a focusing lens each of which is positioned such that laser light entering the laser focusing optics passes, in order, through the input lens, the pinhole screen, the collimating lens, and the focusing lens.

18. The optical probe recited in claim 12, wherein the laser focusing optics are operable to focus the laser beam such that the width (d) of the laser beam is less than or equal to approximately five micrometers (5 μm) at a reflection point on the surface of the wafer.

19. A system, comprising:
laser means for shining a laser beam on a surface of a wafer;
laser light detecting means for detecting laser light reflected from the surface of the wafer in three ranges of angles of reflection; and
translation means for moving the laser light detecting means adjacent the surface of the wafer; and
wherein the laser light detection means includes:
a diffuse light detector and a diffuse light director directing only diffuse reflected laser light from the surface of the wafer to the diffuse light detector;
a near specular light detector and a near-specular light director directing only near-specular reflected laser light from the surface of the wafer to the near-specular light detector; and
a specular light detector and a specular light director directing only specular reflected laser light from the surface of the wafer to the specular light detector.

20. The system recited in claim 19, further comprising wafer rotation means for rotating the wafer.

21. The system recited in claim 19, further comprising computing means for processing signals from the laser light detecting means.

22. The system recited in claim 19, further comprising a chamber, wherein the laser light detecting means is located within the chamber.

23. The system recited in claim 19, further comprising wafer rotation means for rotating the wafer and a chamber, wherein the wafer rotation means and the translation means are located within the chamber.

24. The system recited in claim 19, further comprising wafer rotation means for rotating the wafer and a chamber, wherein the wafer rotation means, the translation means and the laser light detecting mean are located within the chamber.

25. The system recited in claim 19, wherein the laser light detecting means includes the laser means.

26. The system recited in claim 19, wherein the laser light detecting means includes the laser means and focusing means for focusing the laser beam on the surface of the wafer.

27. The system recited in claim 19, wherein the translation means moves the laser light detecting means adjacent the surface of the wafer.

28. An optical probe, comprising:
a housing;
a laser directing mechanism within the housing operable to direct a laser beam to a surface of a wafer positioned adjacent the housing; and
a laser light detection mechanism located within the housing and operable to detect laser light reflected from the surface of the wafer in three ranges of angles of reflection; and
wherein the laser light detection mechanism includes:
a diffuse light detector and a diffuse light director directing only diffuse reflected laser light from the surface of the wafer to the diffuse light detector;
a near specular light detector and a near-specular light director directing only near-specular reflected laser light from the surface of the wafer to the near-specular light detector; and
a specular light detector and a specular light director directing only specular reflected laser light from the surface of the wafer to the specular light detector.

* * * * *